United States Patent [19]

Janzen

[11] 4,286,881
[45] Sep. 1, 1981

[54] SAMPLE CELL
[75] Inventor: Jay Janzen, Bartlesville, Okla.
[73] Assignee: Phillips Petroleum Company, Bartlesville, Okla.
[21] Appl. No.: 15,397
[22] Filed: Feb. 26, 1979
[51] Int. Cl.³ .......................................... G01N 21/01
[52] U.S. Cl. ..................................... 356/440; 352/244
[58] Field of Search ............... 356/244, 409, 432, 436, 356/440, 442; 250/227

[56] References Cited
U.S. PATENT DOCUMENTS

| 3,305,689 | 2/1967 | Leavy et al. | 250/227 |
| 3,679,315 | 7/1972 | Laucournet et al. | 356/409 |
| 3,810,695 | 5/1974 | Shea | 356/73 |
| 3,891,325 | 6/1975 | Schuster et al. | 356/440 |
| 3,963,351 | 6/1976 | Chance et al. | 250/227 |
| 3,999,860 | 12/1976 | Demsky et al. | 356/244 |
| 4,066,362 | 1/1978 | Carter | 356/440 |

FOREIGN PATENT DOCUMENTS

| 1959612 | 6/1971 | Fed. Rep. of Germany | 356/432 |
| 2133797 | 1/1973 | Fed. Rep. of Germany | 356/436 |
| 2272378 | 12/1975 | France | 356/432 |

Primary Examiner—R. A. Rosenberger

[57] ABSTRACT

A sample cell with at least one movable lens is provided for spectrophotometric study.

7 Claims, 3 Drawing Figures

SAMPLE CELL

BACKGROUND OF THE INVENTION

The invention relates to an apparatus for forming and containing semi-solid samples of reproducible thickness for the performing of optical measurements thereon. In another aspect, the invention relates to a method for taking optical measurements of a semi-solid sample.

In colorimetric and spectrophotometric studies, sample containers are required for holding the samples to be studied. The sample containers provided by the prior art were not well adapted for the study of semi-solid samples which include, for example, gels, amorphous polymers, and highly viscous liquids. Semi-solid samples do not flow as readily as the liquids for which the cells provided by the prior art were designed. Because of this, it was difficult to force semi-solid samples to fit into the contours of prior art cells to obtain reproducible sample dimensions. It has thus been difficult to obtain samples of semi-solid materials having reproducible thickness by utilizing the sample cells of the prior art. Difficulties were also encountered in obtaining bubble-free samples, and also in cleaning the sample cells after use. For quantitative studies of the optical properties of semi-solid materials, it is thus extremely desirable to have an easy-to-clean apparatus for producing bubble-free semi-solid samples of reproducible thicknesses.

OBJECTS OF THE INVENTION

It is thus an object of this invention to provide a sample cell suitable for use with semi-solid samples which produces bubble-free specimens of reproducible thickness.

It is a further object of this invention to provide a sample cell suitable for use in studying colorimetric and spectrophotometric properties of semi-solid samples.

It is another object of this invention to provide a sample cell for use with semi-solid samples which is simple and requires little maintenance.

It is yet another object of this invention to provide a method for taking optical measurements of semi-solid materials.

SUMMARY OF THE INVENTION

According to the invention, a sample cell comprises two lenses with a sample area therebetween with at least one of the lenses being movable with respect to the other so that a semi-solid sample may be placed in the sample area and squeezed to a predetermined thickness. Further according to the invention, optical measurements of a semi-solid sample are taken employing the above-described sample cell by transmitting electromagnetic radiation, such as light, from a source through the first lens, the semi-solid sample of predetermined thickness, and the second lens; reflecting the light thus transmitted back through the second lens, the semi-solid sample of predetermined thickness, and the first lens; receiving at least a portion of the light back at a receiving means; and comparing the light transmitted from the source to the light received by the receiving means.

DETAILED DESCRIPTION OF THE INVENTION

Figure 1:
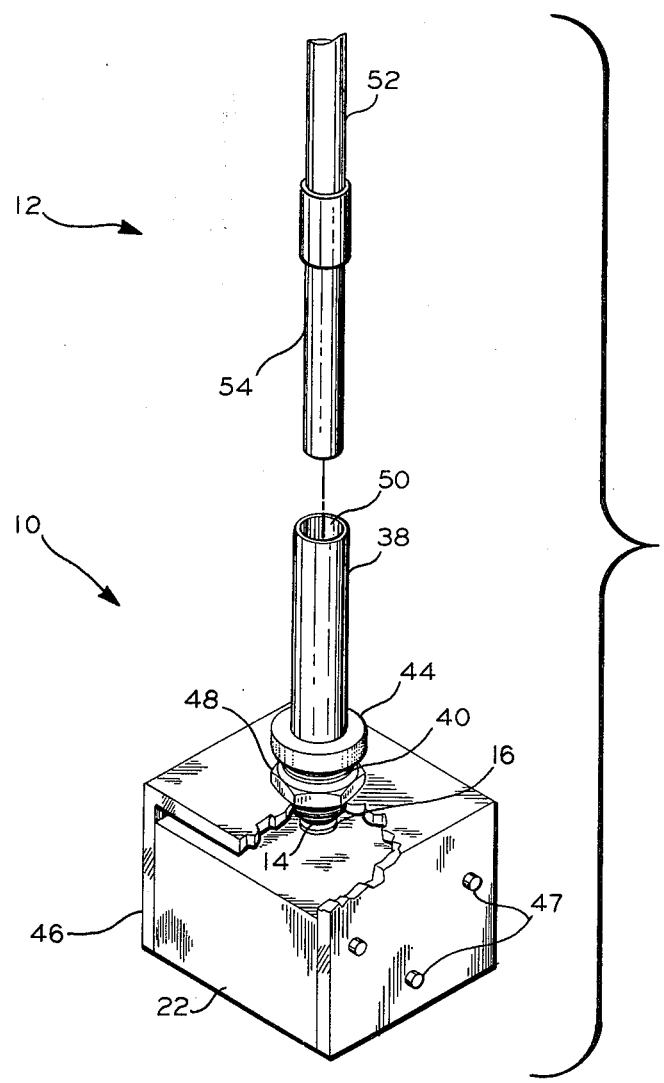
FIG. 1 is a perspective view of a sample cell in accordance with one embodiment of the present invention with part of the housing broken away.
Figure 2:
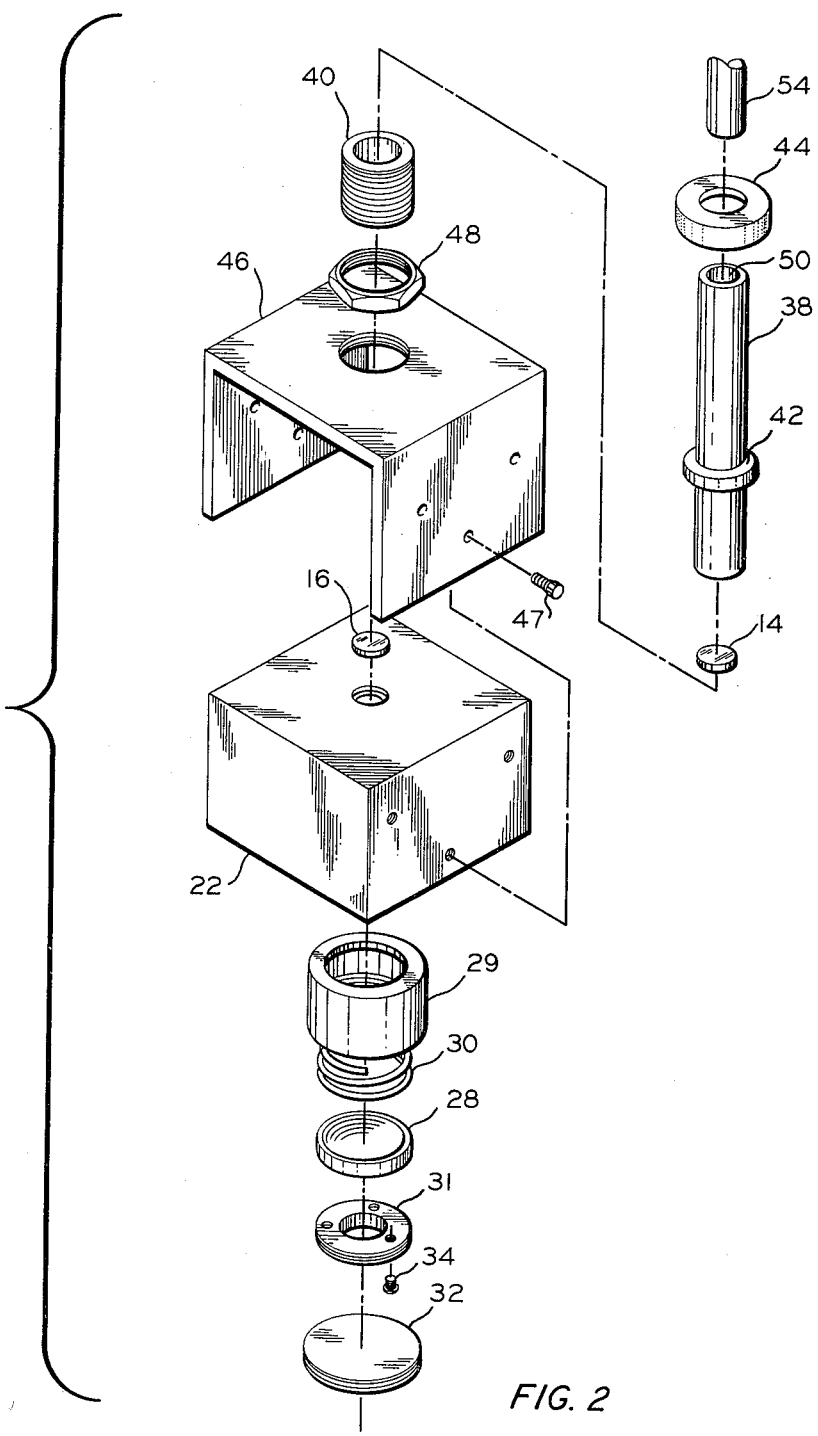
FIG. 2 is an exploded view of the sample cell of FIG. 1.

In FIG. 1 the reference numeral 10 designates generally the sample cell of the present invention. The reference numeral 12 designates generally a fiber optic probe suitable for use with the present invention.

Figure 3:
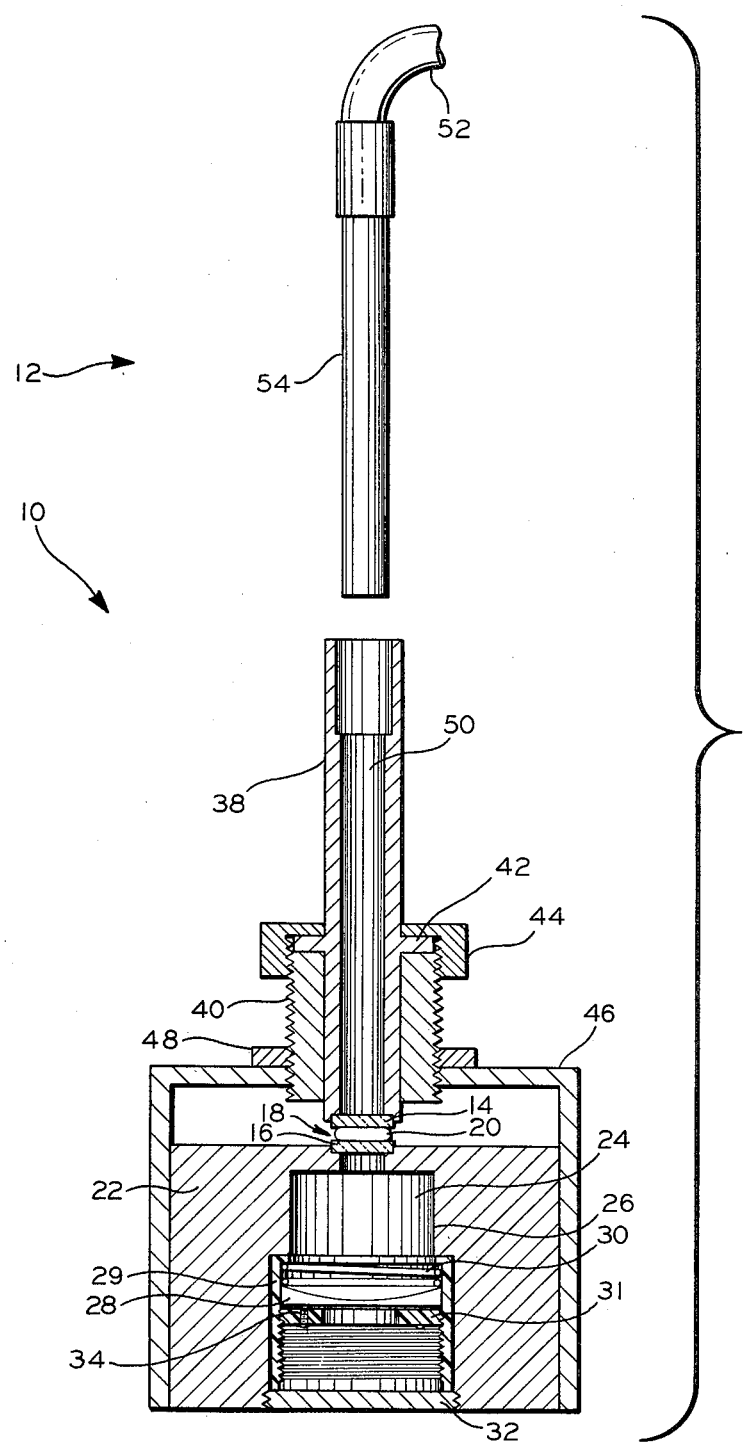
FIG. 3 is a cross-sectional view of the sample cell of FIG. 1.

The apparatus 10 comprises a lens 14 and a lens 16. The lenses 14 and 16 are constructed of a material which is relatively transparent to radiation being utilized in study of a semi-solid material. The lenses can be constructed of any suitable material, such as for example glass, silica or quartz. Preferably, the lenses are flat discs and are identical but they can be of different sizes and shape. The lens 14 and the lens 16 partially define a sample area 18 which, as illustrated in FIG. 3, is at least partially occupied by a sample 20. Lens 16 partially rests on suitable support means such as a block 22. Preferably, the lens 16 is cemented in place in a recess in an upper surface of the block 22 with at least a portion of the lens 16 protruding above the surface of the block 22 toward the lens 14. The block 22 has a passage 24 extending at least partially therethrough and in contact with the lens 16. Passage 24 is defined by an interior surface 26 of the block 22. Reflecting means, such as a mirror 28, is mounted in the passage 24 at a distance from the lens 16 by any suitable mounting means. As illustrated, the mirror 28 rests in a mirror support means which rests on a cap 32. The cap 32 is threadably retained to a portion of the interior surface 26 of the block 22.

The mirror support means is preferably constructed of steel or brass and comprises a tubular member 29 with an annular flange partially closing the upper end. The tubular member 29 has a partially threaded interior surface defining a bore and an outside diameter allowing it to be closely received in passage 24. The mirror 28 is located within the tubular member 29 and extends at least partially across the bore of the tubular member 29. The mirror 28 faces toward the annular flange of tubular member 29. Biasing means, such as spring 30 are located between the mirror 28 and the annular flange. The spring 30 cooperates with the annular flange and the mirror 28 to urge the mirror 28 toward a mirror support ring 31. The mirror support ring 31 has a threaded exterior surface in engagement with the threaded interior surface of tubular member 29. The mirror support ring 31 is thus threadably adjustable within the tubular member 29. Mirror aiming means, such as the screws 34 establish cooperation between the mirror support ring 31 and the mirror 28. There are preferably three screws 34, so as to provide three points of cooperation between mirror support ring 31 and the mirror 28. Each screw 34 has a headed end and a tip end. The mirror 28 is urged against the tip ends of the screws by the spring 30. The screws 34 extend normally through the body of the mirror support ring 31 in threaded bores. By adjustment of the screws 34 in the threaded bores through the mirror support ring, the mirror 28 can be aimed.

The lens 14 is supported by suitable support means at a distance from the lens 16. The distance between the lenses fixes at least one dimension of the sample area 18. As illustrated, the lens 14 support means comprises a tubular member 38 having a first and a second end slidbably mounted adjacent a superstructure 46. The superstructure 46 and the tubular member 38 are preferably constructed of aluminum. The superstructure 46 is mounted to the block 22 by any suitable means, such as by screws 47. The lens 14 is mounted adjacent the second end of the tubular member 38, preferably in a recess and at least partially protruding from the recess toward the lens 16. The lens 14 can be secured in the recess by any suitable means, such as by cementing using optical cement. An interior surface of the tubular member 38 defines a bore 50 suitable for receiving the fiber optic probe 12 which is attached to a colorimeter or the like (not shown) via an optical fiber cable 52. Preferably, the superstructure 46 forms an open ended housing around the lens 14 and the lens 16.

Slidable mounting means, such as a bushing 40, slidably mounts the tubular member 38 to the superstructure 46. Together, the block 22, the superstructure 46, the bushing 40, and the tubular member 38 cooperate to function as a support means to position lens 16 between lens 14 and mirror 28, and to align lens 14, lens 16 and mirror 28 so that a beam of light passing through the lenses is reflected back through the lenses by mirror 28. The bushing 40 is preferably constructed of steel or brass. The bushing 40 is adjustable with respect to superstructure 46 due to its being threadably mounted to the superstructure 46. A lock nut 48 prevents unintentional movement between the bushing 40 and the superstructure 46. The lock nut 48 is preferably constructed of steel or brass. An annular flange 42 mounted intermediate the ends of the tubular member 38 acts to hold the lens 14 a predetermined distance from the lens 16 by abutting against an upper portion of bushing 40. Preferably, the annular flange 42 is integral with the tubular member 38 and is constructed of aluminum. Suitable draw-down means, such as a draw-down nut 44, urge and hold the flange 42 adjacent the upper end of the bushing 40. Preferably, the draw-down nut 44 is constructed of steel or brass. Together, the annular flange 42 and the draw-down nut 44 cooperate to function as squeezing means for squeezing a sample placed in the sample area 18. Preferably, tubular member 38 and bushing 40 are oriented with respect to each other by means such as a key and channel arrangement as is well known to those skilled in the art.

The optical fiber probe 12 comprises a sleeve 54 surrounding a bundle of optical fibers. The sleeve 54 is adapted for closely fitting the bore 50 in the tubular member 38. Preferably, sleeve 54 will only fit into bore 50 in one orientation. It can be secured in the desired orientation by any suitable means such as by cementing with sealing wax. Preferably, the sleeve 54 is constructed of stainless steel. About one-half of the optical fibers within sleeve 54 are adapted for transmitting and emitting electromagnetic radiation and about one-half of the optical fibers are adapted for receiving and transmitting electromagnetic radiation. A suitable probe is available from Brinkmann Instruments, Incorporated of Houston, Texas. The modification comprises merely removing the factory tip from the probe and replacing it with a tip such as the sleeve 54. The sleeve 54 can be secured to the bundle of optical fibers by any suitable means. Preferably, a sealing wax is utilized.

In operation of the present invention, the draw-down nut 44 is disengaged from the bushing 40 and the tubular member 38 at least partially removed from the remainder of the apparatus 10. A sample of semi-solid material is placed onto the lens 16. The tubular member is then lowered through the bushing 40 until lens 14 comes into contact with the sample. The draw-down nut 44 is engaged with the bushing 40 and tightened, so that the distance between the lens 14 and the lens 16 is reduced and any excess semi-solid sample squeezed from the sample area 18 between the two lenses. The distance between the two lenses is precisely controlled by the contact of the annular flange 42 with the bushing 40. The vertical positioning of bushing 40 can be adjusted to obtain samples of whatever thickness is desired. Samples of 0.5 to 5 millimeter thick are preferred, although thiner or thicker samples can be obtained if desired.

As the draw-down nut 44 forces the annular flange 42 into contact with the bushing 40, the sample 20 partially escapes the sample area 18. Due to the elevated position of the lens 16 with respect to the support means 22, the escaped portion of sample 20 protrudes outwardly from sample area 18 or falls downward onto an upper surface of the support means 22 from which it can be easily removed. The portion of the sample 20 which remains in the sample area 18 is sandwiched between the lens 14 and the lens 16 and if this distance is maintained constant for different samples, each sample has a uniform thickness. With each sample positioned as shown for sample 20, a beam of light can be passed through lens 14, the sample 20 and lens 16 so that the absorptivity of each sample can be precisely determined.

As described, the fiber optic probe 12 can be inserted into the tubular member 38 and thus aligned normally to the lens 14, the sample 20, the lens 16 and the reflecting means 28. A desired wavelength of electromagnetic radiation is transmitted as a primary beam through the fiber optic probe 12 and passes through the lens 14, the sample 20, the lens 16 to the reflecting means 28 from where it is reflected back through the lenses and sample and received back into the fiber optic probe 12 for transmission to a detecting means (not shown). By comparison of a property of the light emitted from the fiber optic probe 12 to a property of the light received by the fiber optic probe 12, information can be obtained about the optical characteristics of the sample 20.

Although any type of mirror can be used as the reflecting means 28, the reflecting means 28 preferably comprises a concave spherical mirror. Preferably, the distance between the mirror and the sample will be adjusted relative to the axis of symmetry of the concave mirror so that the intensity of reflected light reaching the fiber optic probe 12 is at a maximum. Normally, this maximum will be achieved when the distance between a portion of the mirror in axial alignment with the lens 14 and the lens 16 is at a distance from the sample approximately equal to the radius of curvature of the mirror. Preferably, the mirror is a front-surfaced silvered mirror.

It is important to remove any residual sample remaining on the lenses of the apparatus between experimental runs. This is easily accomplished by disengaging the draw-down nut 44 from the bushing 40 and at least partially removing the tubular member 38 from the reaminder of the apparatus. The lenses are then easily reached and cleaned with a swab dampened with a suitable solvent. Cleaning is greatly facilitated when the embodiment of the invention employed utilizes protruding lenses. Methanol is the solvent presently preferred.

In the use of the cell, standardization can be accomplished by any suitable means. For example, if the dispersion of carbon black and a given polymer is being studied, a sample of the polymer containing no dispersed carbon black can be used as the reference standard. The sample containing no dispersed carbon black is squeezed between the lenses 14 and 16 to a desired thickness and the absorbance of the standard set at 0 or, alternatively, transmission set at 100 percent. Alternatively, air can be employed as the reference standard once the relationship between the absorptivity of air and polymer sample is established.

What is claimed is:

1. Apparatus comprising
   (a) a reflecting means,
   (b) a first lens;
   (c) a second lens;
   (d) a block with a passage at least partially therethrough with said second lens being at least partially supported by said block in a position at least partially over one end of said passage and said reflecting means being positioned in said passage;
   (e) a superstructure mounted on said block;
   (f) a tubular member having a first end and a second end with said first lens being mounted adjacent the second end of said tubular member, the interior of said tubular member being adapted for receiving a fiber optic probe;
   (g) a slidable mounting means affixed to said superstructure slidably mounted said tubular member adjacent said superstructure, said first lens, said second lens and said reflecting means being in alignment so that a beam of light emitted from a fiber optic probe when received by the interior of the tubular member passes through the first lens, the second lens and is reflected by the reflecting means back through the second lens and the first lens, in that order, to the fiber optic probe, and wherein said first lens at least partially protrudes from adjacent said tubular member toward said second lens and said second lens at least partially protrudes from said block towards said first lens;
   (h) a sample area having at least one dimension fixed by the distance between said first lens and said second lens; and
   (i) squeezing means suitable for squeezing a sample positioned in the sample area between the first lens and the second lens to a predetermined thickness.

2. Apparatus as in claim 1 wherein said squeezing means comprises:
   (a) an annular flange affixed to said tubular member intermediate the first and second ends thereof and adapted to abut against said slidable mounting means; and
   (b) draw-down means cooperating with said annular flange and said slidable mounting means to draw said annular flange down into contact with said slidable mounting means.

3. Apparatus as in claim 2 wherein said slidable mounting means is adjustable with respect to said superstructure.

4. Apparatus as in claim 3 wherein: said reflecting means comprises a concave spherical mirror.

5. A method for taking optical measurements of a semi-solid material comprising:
   (a) placing a sample of material into contact with a first protruding lens;
   (b) moving a second protruding lens into contact with the sample;
   (c) squeezing a portion of the sample to a predetermined thickness between the first lens and the second lens by moving the second lens;
   (d) providing a primary beam of electromagnetic radiation normal to said lens;
   (e) transmitting at least part of the primary beam through the first lens, the sample portion and the second lens;
   (f) reflecting at least part of the transmitted primary beam back through the second lens, the sample portion and the first lens in that order; and
   (d) comparing a property of the reflected beam to a property of the primary beam.

6. A method as in claim 5 wherein the sample is squeezed to a predetermined thickness of between about 0.5 and about 5 millimeters.

7. Apparatus comprising
   (a) a reflecting means,
   (b) a first lens;
   (c) a second lens;
   (d) a block with a passage at least partially therethrough with said second lens being at least partially supported by said block in a position at least partially over one end of said passage and said reflecting means being positioned in said passage;
   (e) a superstructure mounted on said block;
   (f) a tubular member having a first end and a second end with said first lens being mounted adjacent the second end of said tubular member, the interior of said tubular member being adapted for receiving a fiber optic probe;
   (g) a slidable mounting means affixed to said superstructure slidably mounting said tubular member adjacent said superstructure, said first lens, said second lens and said reflecting means being in alignment so that a beam of light emitted from a fiber optic probe when received by the interior of the tubular member passes through the first lens, the second lens and is reflected by the reflecting means back through the second lens and the first lens, in that order, to the fiber optic probe;
   (h) a sample area having at least one dimension fixed by the distance between said first lens and said second lens; and
   (i) squeezing means suitable for squeezing a sample positioned in the sample area between the first lens and the second lens to a predetermined thickness.

* * * * *